Figure 1:
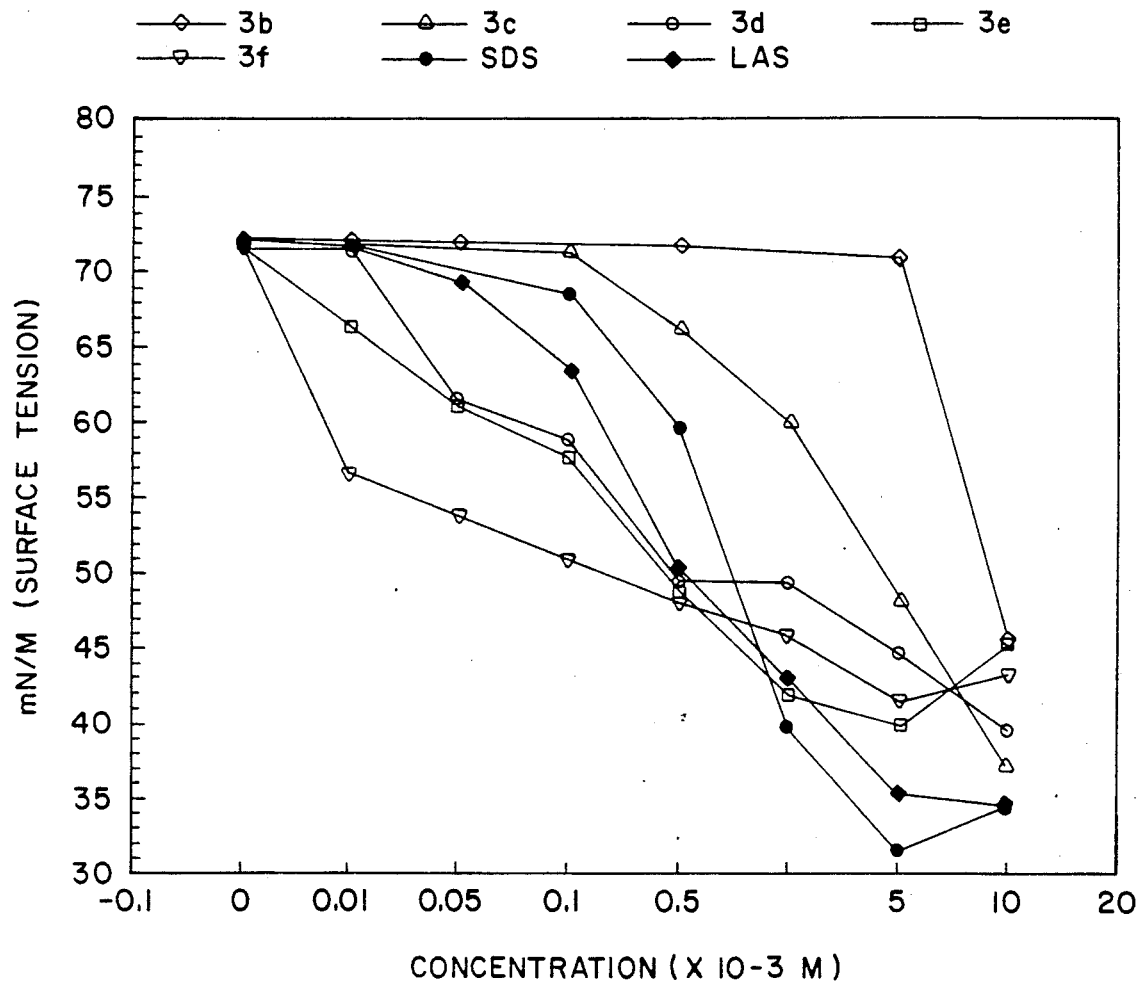

United States Patent [19]

Kotick

[11] Patent Number: 5,049,699

[45] Date of Patent: Sep. 17, 1991

[54] REGIOSELECTIVE SYNTHESIS OF MONO-ALKYL CITRIC ACID ESTERS

[75] Inventor: Michael P. Kotick, Elkhart, Ind.

[73] Assignee: Haarmanns' Reimer Corp, Springfield, N.J.

[21] Appl. No.: 468,171

[22] Filed: Jan. 22, 1990

[51] Int. Cl.[5] .............................................. C07C 69/66
[52] U.S. Cl. .................................. 560/180; 549/232; 549/296
[58] Field of Search ................. 560/180; 549/232, 296

[56] References Cited

U.S. PATENT DOCUMENTS

| | | | |
|---|---|---|---|
| 699,422 | 5/1902 | Sternberg | 549/296 |
| 858,142 | 6/1907 | Berendes et al. | 549/296 |
| 858,143 | 6/1907 | Berendes et al. | 549/296 |
| 874,824 | 12/1907 | Berendes et al. | 549/296 |
| 921,944 | 5/1909 | Berendes et al. | 549/296 |
| 2,518,678 | 8/1950 | Gooding et al. | 260/484 |
| 3,135,769 | 6/1964 | Besso | 549/296 |
| 3,763,189 | 10/1973 | Harken | 549/296 |
| 4,866,202 | 9/1989 | Weil | 560/180 |

FOREIGN PATENT DOCUMENTS

| | | | |
|---|---|---|---|
| 186659 | 3/1906 | Fed. Rep. of Germany | 549/296 |
| 959412 | 6/1964 | United Kingdom | 560/180 |

OTHER PUBLICATIONS

Lee and Miller, J. Org. Chem., 1983, 48, 24–31.

Primary Examiner—Bruce Gray
Attorney, Agent, or Firm—Jerome L. Jeffers

[57] ABSTRACT

Disclosed are 1- and 2-mono esters of citric acid and methods for preparing them in the pure form. These novel compounds are useful as surfactants.

3 Claims, 2 Drawing Sheets

REGIOSELECTIVE SYNTHESIS OF MONO-ALKYL CITRIC ACID ESTERS

BACKGROUND OF THE INVENTION

The esterification of citric acid with varying molar ratios of long chain fatty alcohols can yield the mono-, di-, or tri- ester depending upon the molar ratio of the reactants. For example, EPO Published Application 0 199 131 reveals that citric acid may be esterified with one, two or three mole equivalent of ethoxylated long chain alcohols to yield products which consist mainly of mono-, di-, or tri- esters. The reaction of one mole of citric acid with about 2 moles of a long chain fatty alcohol yields mixtures of mono-, di-, and tri- ester compounds (U.S. Pat. No. 2,518,678). It is difficult to isolate the desired pure mono- or di- esters from these mixtures because of their similar solubility characteristics.

It is generally agreed that the predominant mono-ester product produced from the esterification of citric acid is the unsymmetrical 1-mono ester, while the predominant di-ester obtained is the 1,3 symmetrical product. Procedures have not been reported which reveal how to obtain the kinetically unfavored 2- mono substituted esters. Such a method has now been found. Likewise, there has been discovered a method to regioselectively prepare 1- mono substituted citric acid esters, free of other isomers. It is advantageous to have a method which can selectively prepare quantities of 1- or 2- citric acid mono ester compounds in the pure state so that their physical-chemical attributes can be assessed. Selectively substituted citric acid esters can also serve as building blocks for other synthetic studies.

The present invention involves the regioselective preparation of 1- and 2- mono substituted citric acid esters and the use of such esters as surface active agents.

Claims have been made for the use of partially esterified citric acid derivatives as:

Surfactants: Japan Patent 64-22336 (1989) Citric acid di-ester mono-salt as an anionic surfactant for detergents with reduced foaming and good penetration properties. EPO: 86104119.2 (1986) Surfactants derived from citric acid and aliphatic polyoxyalkylated alcohols: Borchert and Hartford, Proceedings World Surfactant Congress. "Surfactants in Our World - Today and Tomorrow". 1984, Munich, West Germany, Volume II. p. 147. Compositions consisting mainly of citric acid di-esters as surfactants. CA 92:997002.

It is generally recognized that the uncatalyzed or acid catalyzed reaction of citric acid with excess molar quantities of alcohols yields primarily the unsymmetrical 1-substituted compounds as the kinetic product. Lee and Miller report in J. Org. Chem., 1983, 48, 24 that the product of the reaction of anhydromethylene citric acid, as the di-triethylammonium salt, with short chain alcohols, i.e. C-1 to C-3 carbon atom alkyl alcohols and benzyl alcohol, in refluxing chloroform, yields only the symmetrical 2-mono ester. Anhydromethylene citric acid is prepared by the fusion of citric acid and paraformaldehyde.

SUMMARY OF THE INVENTION

The present invention involves 1- or 2- mono esters of citric acid characterized by the formula:

$$\begin{array}{c} CH_2-COO(H \text{ or } Y) \\ HO-\!\!\!\!-COO(H \text{ or } Y) \\ CH_2-COOH \end{array}$$

where Y is an alkyl chain of the formula $-(CH_2)_n CH_3$ with n being a number of from 7 to 19. These esters are prepared by the reaction of anhydromethylene citric acid with an alcohol of the formula $HO-(CH_2)_n CH_3$.

DESCRIPTION OF THE INVENTION

The preparation of the presently claimed citric acid esters is illustrated by Scheme I.

SCHEME I

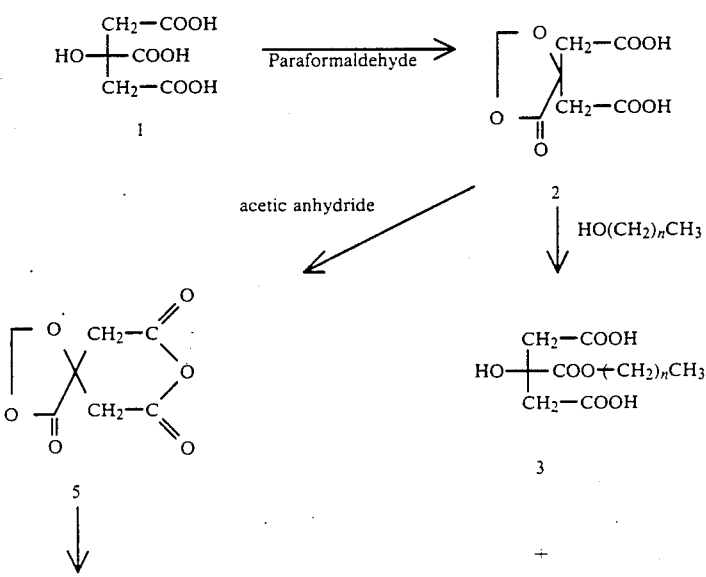

SCHEME I

-continued

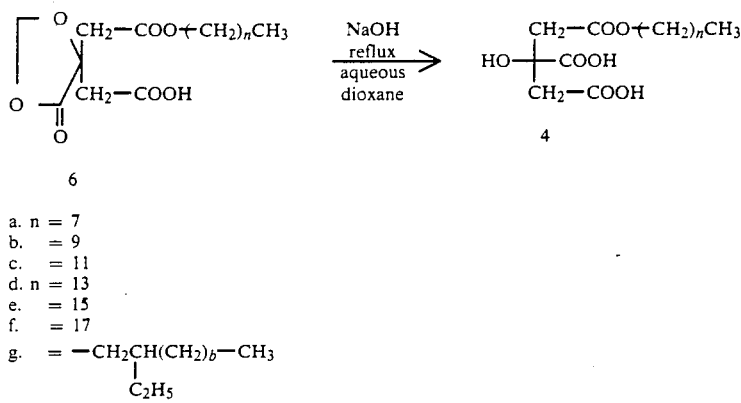

4

- a. n = 7
- b.    = 9
- c.    = 11
- d. n = 13
- e.    = 15
- f.    = 17
- g.    = —CH$_2$CH(CH$_2$)$_b$—CH$_3$
         |
         C$_2$H$_5$

Referring to Scheme I, citric acid is reacted with paraformaldehyde in a suitable solvent to form anhydromethylene citric acid 2 which is reacted with a straight or branched long chain alcohol of the formula HO—(CH$_2$)$_n$CH$_3$ where n is from 7 to 19. This reaction, which is carried out in a solvent such as chloroform, ethyl acetate,--acetonitrile or dioxane at a temperature of from about 65° to 110° C., provides the symmetrical 2-mono ester of the alcohol, 3 as well as about 10% of the 1-substituted ester 4. Investigation of the reaction product of 2- with long chain alcohols indicated that the predominant product is the symmetrical 2-mono ester, compound 3. The structure of this product is apparent from the NMR spectra which shows a symmetrical quartet for the methylene protons of the citric acid moiety. In addition, the 13-C spectra indicates that the carbonyl groups in the molecule are present in a 1:2 ratio as would be expected from a symmetrical citric acid derivative. The amount of 4 in the reaction mixture appears to increase as the reaction period is extended or as the chain length of the reacting alcohol is increased. However, in most cases, the symmetrical 2-mono ester 3 can be obtained in the pure state by crystallization of the reaction product from toluene.

Methods for the preparation of 1-mono substituted citric acid esters 4 generally yield mixtures of compounds. It has been discovered that compounds 4 may be prepared, free of the contaminating 2-mono ester, by a multi step approach. Reaction of 2 with acetic anhydride on a steam bath gives a good yield of the anhydride 5. This reacts, albeit in low recoverable yield, with an excess of alcohol to give the 1-mono substituted derivative 6. Cleavage of the blocking methylene group is accomplished by refluxing the mono-sodium salt of 6 in aqueous dioxane to provide the crystalline unsymmetrical mono-esters 4 in good yield. The complexity of the NMR spectra in the region--of the citric acid methylene groups confirms the identity of these compounds 4 as 1-substituted derivatives. In these cases, the methylene protons are observed as a complex multiplet between 2.87 and 2.61 ppm. In addition, the 13-C spectra showed three distinct carbonyl groups in an apparent 1:1:1 ratio.

The mono esters prepared herein can also be distinguished on the basis of the mass spectrum of their trimethylsilyl derivatives. The correct M-15 peak was quite strong for all the mono esters. The 2-substituted derivatives 3 had fragmentation patterns in which the four largest peaks were (m/z): 73, 273, 147 and 363. In contrast, the 1-substituted derivatives showed major fragmentation peaks with m/z at 73, 201, 147 and 273. While the order of the largest peaks varied in some cases, the presence of a 363 peak is characteristic of the 2-substituted derivatives 3 while the 1-substituted derivatives 4 have a characteristic fragment at 201.

The following examples illustrate the synthesis and utility of the compounds prepared as described above.

EXAMPLE I

A. Preparation of Anhydromethylene Citric Acid (2)

Anhydrous citric acid (1), (120 g, 0.625 mole) and paraformaldehyde (21 g, 0.70 mole) were mixed in a beaker which was then immersed in an oil bath preheated to 145° C. The mixture, with intermittent stirring, was held at this temperature for 2 hours. The mixture melted, then resolidified during this time. The cooled mixture was dissolved in a minimal amount of boiling water on the hot plate (total volume ≈225 ml). On cooling, crystals formed. The mixture was kept overnight in the refrigerator, then, the crystals were collected, washed with cold water and dried on the filter using a heat lamp to give 2 (69 g, 53%) as white crystals, mp 205°-207° C.

Preparation of 2-Monooctyl Citric Acid (3a)

To a suspension of 2 (50.0 g, 0.245 mole), in ethanol-free chloroform (500 ml), was added triethylamine (75 ml, 0.538 mole) followed by octanol (80 ml. 0.508 mole). The resulting solution was refluxed for 45 hours, cooled and the chloroform removed by evaporation at 40° C. The residue was dissolved in ethyl acetate (400 ml) and this solution washed 3 times with cold saturated sodium bicarbonate solution (200 ml). The combined bicarbonate extract was washed twice with ethyl acetate (200 ml). The bicarbonate extract was then adjusted to pH 2 by the drop wise addition of concentrated HCl (≈78 ml). The cloudy solution was extracted with three portions of ethyl acetate (200 ml), the combined ethyl acetate extract dried (magnesium sulfate), filtered and evaporated, finally in high vacuum at 50° C. to give 3a (61.7 g, 90%) as an oil. The oil was dissolved in 200 ml of hot toluene on the steam bath and filtered from some insoluble material. The filtrate was kept at room temperature overnight, then, the crystals were collected, washed with toluene and dried to give 3a (43.09 g, 58%), mp 65.8°-66.7° C.

The mother liquor was shown to contain by TLC, in addition to the major isomer, the presence of a slower moving isomer. The major isomer had an Rf of about 0.5 while the minor isomer had Rf 0.4. The crude reaction mixture prior to work up, (after derivatization with BSTFA) showed by GC about a 10:1 mixture of the mono-esters with Rt 8.17 and 8.27 minutes, respectively. The crystalline 2-mono ester 3a showed a single peak with Rt 8.17 minutes under the same conditions.

Material prepared in another reaction was recrystallized from toluene to give an analytical sample of 3a, mp 65.2°–65.9° C.

Anal. Calcd for $C_{14}H_{24}O_7$ (304.3): C, 55.25; H, 7.95. Found: C. 55.25; H, 7.94.

2-Monododecyl Citric Acid (3b)

A mixture of 2 (50 g), triethylamine (75 ml) and decanol (110 ml) in ethanol-free chloroform (500 ml) was refluxed for 42 hours. GC analysis indicated a 10:1 mixture of the 2- and 1-monodecyl ester in addition to about 9% of unreacted starting material. Processing as indicated above gave the crude product (69.6 g, 86%) as an opalescent oil. This oil was dissolved in hot toluene (200 ml) on the steam bath, filtered from a small amount of insoluble material, which was washed with two additional portions of hot toluene (50 ml) and the combined filtrates cooled at room temperature.

After standing overnight, the crystals which formed were collected, washed with toluene and dried on the filter to give 46.1 g of 3b, mp 75.4°–76.1° C., containing a trace of the 1-isomer as indicated by TLC. Recrystallization of a portion of this material from toluene gave an analytical sample of 3b, mp 75.6°–76.6° C., which migrated as a single isomer on TLC and GC.

Anal. Calcd, for $C_{16}H_{29}O_7$ (332.4): C, 57.82; H, 8.49. Found: C, 57.69; H, 8.47.

2-Monododecyl Citric Acid (3c)

A mixture of 2 (10 g), triethylamine (15 ml) and dodecanol (22 ml) in ethanol-free chloroform (100 ml) was refluxed for 22 hours. Workup in the usual fashion gave the crude product (15.3 g, 86%) as a semi-solid. GC analysis indicated the mixture contained an 89:6 mixture of the major and minor isomers together with about 4% of unreacted 2. Crystallization of this material gave 11.8 g of 3c with mp 74.8°–75.6° C. Recrystallization gave 3c with mp 74.7°–75.3° C., which migrated as a single spot on TLC and as a broad peak, Rt 10.88–10.93, by GC, after derivatization.

Anal. Calcd for $C_{18}H_{32}O_7$ (360.5): C, 61,83; H, 9.34. Found: C, 61.95; H, 9.33.

The 2-mono-hexadecyl ester 3e and the octadecyl ester 3f were prepared in a similar manner with the exception that all extractions were done using chloroform: Compound 3e was obtained in 73% yield with mp 87.8°–88.8° C.; recrystallizated from toluene it had mp 88.0°–89.3° C. Compound 3f was obtained in 68% yield, mp 89.6°–90.8° C., which has mp 90.1°–91.0° C., on recrystallization from toluene. Compound 3g was obtained in 55% yield with mp 81.4°–82.4° C. Recrystallization from toluene gave material with mp 80.4°–80.9° C.

C. Preparation of Anhydromethylene Citric Acid Anhydride (5)

To a mixture of 2 (50.0 g) and acetic anhydride (200 ml) was added concentrated sulfuric acid (1.0 ml). The resulting suspension was heated on the steam bath for 3 hours. On cooling the reaction mixture in an ice bath for several hours, crystals formed. The residue was diluted with chloroform (500 ml) and further chilled. The crystals were collected, washed with chloroform and dried on the filter to give 5 (39.6 g, 87%), m.p. 154.3°–156.0° C., which was used without further purification for the preparation of 6.

D. Preparation of Anhydromethylene Citric Acid 1-Monoesters (6)

A mixture of -5 (20 g), the appropriate fatty alcohol (100 g) and N,N-dimethylformamide (100 ml) were stirred at 110° C. in a pre-heated oil bath for 3 hours. The cooled solution was evaporated in high vacuum at 70° C. The residue was dissolved in ethyl acetate (500 ml) and the dark solution extracted twice with water. The ethyl acetate solution was then extracted three times with saturated sodium bicarbonate solution (150 ml). The bicarbonate extracts were washed once with ethyl acetate, then adjusted to pH 2 by the addition of concentrated HCl. The acidic solution was extracted with three portions of ethyl acetate (200 ml), the ethyl acetate solution back washed once with water, dried over magnesium sulfate and evaporated. Drying in high vacuum was followed by crystallization of the residue from 50% aqueous ethanol (5a) or absolute ethanol (5d, 5e) to give compounds 5- with the following melting points and yields: 5a, mp 122.1°–123.5° C., 30%; 5d mp 124.8°–125.3° C. 32%; 5e, mp 123.4°–124.6° C., 18%. TLC indicated the presence of trace impurities.

E. Preparation of 1-Monoalkyl Citric Acid Esters (4)

A suspension of 6 (5 g) in dioxane (50 ml)-water (50 ml), containing one equivalent of 1N NaOH was refluxed for 5 to 7 hours. The cooled solution was acidified by the addition of 2 equivalents of 1 N HCl and the solution extracted with three portions of ethyl acetate (100 ml). The combined ethyl acetate extract was back washed with water, dried and evaporated to give a residue which solidified on standing. The residue was crystallized from toluene to give 4 with the following melting points and yields: 4a, mp 90.1°–91.1° C., 84%; 4d, mp 102.7°–103.4° C., 87%; 4e, mp 105.8°–106.2° C., 83%. recrystallization from toluene raised the melting point, however, the products still contained a trace of a very fast moving impurity as indicated by TLC, GC studies indicated homogeneity was greater than 98%.

EXAMPLE II

The utility as surfactants of the above described compounds was determined as follows:

Surface tension measurements were made by 363 suspending the test compound ($1 \times 10^{-3}$ M) in water and adjusting the pH to 9 by the addition of NaOH. Appropriate dilutions were made from this stock solution. Studies by GC showed that the esters were stable to hydrolysis at this pH for greater than 4 hours.

Measurement of the surfactant properties of these compounds revealed that the short chain compounds 3a–3c; 4a did not possess surface activity lowering potential. However, the sodium salts of the longer chain derivatives had surface tension lowering potential in the range of sodium dodecyl sulfate (SDS) and alkylbenzene sulfonates (LAS, Bio-Soft D-62). For the 2-mono substituted series 3, tetradecyl 3d and hexadecyl 3e were more surface active at lower concentrations than the reference compounds, SDS and LAS. The octadecyl compound 3f was the most potent of the series in reducing surface tension. However, its low water solubility, even as the sodium salt, precluded it from further consideration in wash tests. The surface tension properties of the 2-mono alkyl citric acids are schematically illustrated in FIG. 1.

Figure 2:
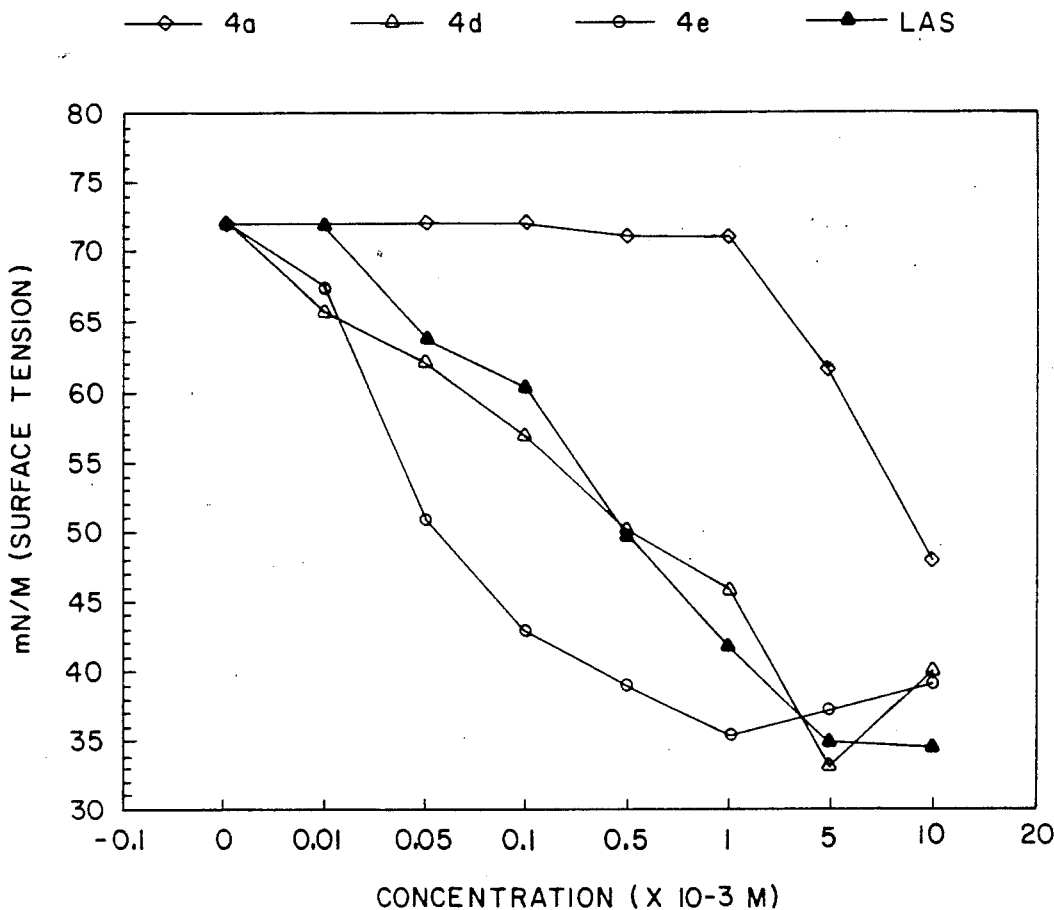

FIG. 2 illustrates the surface lowering properties of the 1-mono alkyl citric acids. Referring to FIG. 2 it can be determined that compound 4d was as active as reference compound LAS in reducing surface tension. The hexadecyl compound 4e had the most potent surface tension reducing ability of these new compounds. It can be determined from the figures that at low concentrations the more active compounds of this series have more surface tension lowering potential with steeper slopes than the reference compounds.

The foregoing results prompted the investigation of the use of these compounds in wash tests. For comparative purposes, a standard liquid detergent formulation, using alkylbenzene sulfonate (LAS, Bio-Soft D-62) was formulated. This standard formulation consisted of 30% of the LAS, 12% sodium xylene sulfonate and 5% sodium sulfate, adjusted to pH 9 with triethanolamine and distilled water to 100%. This standard liquid detergent formulation, 2.0 g, was used in each Terg-0-Tometer pot. The Terg-0-Tometer pot contained 1000 ml of water, 150 ppm water hardness (2:1 Ca:Mg) and had a final pH of 7.4. For the test compounds, 0.6 g of the test compound, 0.24 g of sodium xylene sulfonate, and 0.1 g of sodium sulfate was added directly to the Terg-0-Tometer pot, containing 1000 ml of water, 150 ppm water hardness (2:1 Ca:Mg) and the resulting solution adjusted to pH 7.4 with 1. N sodium hydroxide solution. Wash conditions were 100 degrees F, 10 minute wash cycle followed by a 10 minute rinse with distilled water. The following stained cloth types (Scientific Services, Oakland, NJ) were used: ground-in-clay on cotton, ground-in-clay on cotton/polyester, dust-sebum on cotton and dust-sebum on cotton/polyester. Two Tergo-o-Termeter runs for each surfactant formulation were performed. Reflectance was measured on a Hunter Reflectometer and the percent of soil removed was calculated. The averages from two runs are set out in Table 2.

TABLE 2

| Compound | PERCENTAGE OF SOIL REMOVAL | | | | | | |
|---|---|---|---|---|---|---|---|
| | 3a | 3b | 3d | 3e | LAS | 4d | 4e |
| Soil/Cloth* | | | | | | | |
| C/C | 30 | 26 | 37 | 43 | 42 | 40 | 48 |
| C/CP | 36 | 34 | 46 | 58 | 55 | 40 | 51 |
| DS/C | 14 | 17 | 29 | 43 | 36 | 26 | 44 |
| DS/CP | 3 | 1 | 28 | 32 | 25 | 12 | 39 |
| Total | 83 | 76 | 146 | 179 | 158 | 117 | 180 |

*Soil Types: C = Clay, DS = Dust-Sebum
Cloth Types: C = Cotton, CP = Cotton-Polyester

What is claimed is:

1. A method for the preparation of pure 1-mono esters of citric acid characterized by the formula:

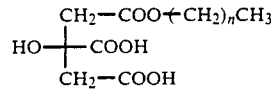

where $(CH_2)_n$ is an alkyl group of 7 to 19 carbon atoms, which method involves the steps of:
   (a) reacting citric acid with paraformaldehyde to form anhydromethylene citric acid;
   (b) reacting the anhydromethylene citric acid with acetic anhydride to form the corresponding anhydride;
   (c) reacting the corresponding anhydride with an alcohol of the formula $HO(CH_2)_nCH_3$ where n is as defined above to form the corresponding 1-mono substituted derivative; and
   (d) refluxing the 1-mono substituted derivative with 1 equivalent of base in aqueous dioxane to provide the desired 1-mono ester of citric acid as characterized by the above formula.

2. The method of claim 1 wherein n is 7, 9, 11, 13, 15 or 17.

3. The method of claim 1 wherein n is 15.

* * * * *